United States Patent [19]

Chiyomaru et al.

[11] 4,303,653
[45] Dec. 1, 1981

[54] ORGANIC PHOSPHORIC ACID ESTER DERIVATIVES, A PROCESS FOR PREPARING THE SAME AND INSECTICIDAL, MITICIDAL OR NEMATOCIDAL COMPOSITIONS CONTAINING THE SAME

[75] Inventors: Isao Chiyomaru; Hidetoshi Sugiyama, both of Shimizu; Koyata Niita, Fujieda; Kunihiko Fujimori, Shimizu; Tadayoshi Hirano; Osamu Tada, both of Shizuoka, all of Japan

[73] Assignee: Kumiai Chemical Industry Co., Ltd., Tokyo, Japan

[21] Appl. No.: 163,662

[22] Filed: Jun. 27, 1981

[30] Foreign Application Priority Data

Jun. 27, 1979 [JP] Japan .................................. 54-80236

[51] Int. Cl.³ .................. C07D 311/70; C07D 311/04; A61K 31/665
[52] U.S. Cl. .................. 424/203; 260/345.2
[58] Field of Search ...................... 260/345.2; 424/203

[56] References Cited

U.S. PATENT DOCUMENTS 4,194,029 3/1980 Lam .................................. 260/345.2

Primary Examiner—Nicky Chan
Attorney, Agent, or Firm—Sughrue, Mion, Zinn, Macpeak and Seas

[57] ABSTRACT

Organic phosphoric acid ester derivatives represented by the formula (I):

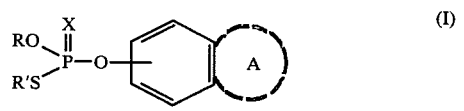

wherein R and R', which may be the same or different, each represents an alkyl group, and A represents a group of atoms necessary to complete together with the two carbon atoms to which they are attached, a 6-membered heterocyclic group containing an oxygen atom as a heteroatom; a process for preparing the same and insecticidal, miticidal or nematocidal compositions containing the same as an active ingredient are disclosed; the compositions exhibit a high ability to control insect pests, mites, nematodes and unhygienic insects harmful to agricultural and horticultural crops.

9 Claims, No Drawings

ORGANIC PHOSPHORIC ACID ESTER DERIVATIVES, A PROCESS FOR PREPARING THE SAME AND INSECTICIDAL, MITICIDAL OR NEMATOCIDAL COMPOSITIONS CONTAINING THE SAME

BACKGROUND OF THE INVENTION

1. Field of the Invention

This invention relates to an organic phosphoric acid ester derivatives, to a process for preparing the same, and to an insecticidal, miticidal or nematocidal composition containing the same as an active ingredient.

2. Description of the Prior Art

Various organic phosphoric acid esters having a pesticidal activity have been reported, for example, in U.S. Pat. No. 3,833,691, German Patent Application (OLS) No. 2,439,663, Japanese Patent Application (OPI) No. 13537/1975, etc.

Development of new pesticides having a wide spectrum and a quite new or unique chemical structure is desired since it is generally expected that most vermin would acquire resistance to pesticides sooner or later.

SUMMARY OF THE INVENTION

One object of the present invention is to provide organic phosphoric acid ester derivatives which have excellent insecticidal, miticidal or nematocidal activities.

A further object of the present invention is to provide a process for preparing the organic phosphoric acid ester derivatives.

Still a further object of the present invention is to provide an effective insecticidal, miticidal or nematocidal composition.

According to one embodiment of this invention an organic phosphoric acid ester derivative represented by the formula (I):

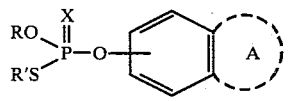

wherein R and R' each represents an alkyl group; X represents an oxygen atom or a sulfur atom; and A represents a group of atoms which are necessary to complete, together with the two carbon atoms to which they are attached, a 6-membered heterocyclic ring containing an oxygen atom as a hetero atom, which ring may be substituted with 1 to 5 alkyl groups.

In another embodiment, this invention provides a process for preparing organic phosphoric acid ester derivatives of the formula (I) above which comprises reacting an O-alkyl-S-alkyl thiophosphoric halide represented by the formula (II):

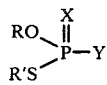

wherein Y represents a halogen atom and R, R' and X are as defined above, with a compound represented by the formula (III):

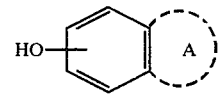

wherein A is as defined above.

In an even further embodiment, this invention provides an insecticidal, miticidal or nematocidal composition comprising an effective amount of at least one compound of the above formula (I) and one or more agriculturally acceptable adjuvants.

DETAILED DESCRIPTION OF THE INVENTION

Various organic phosphorus compounds have been synthesized and intensive physiological tests have been performed as a result of which it has been found that the compounds of the formula (I) exhibit a high ability to control various insect pests, mites nematodes and unhygienic insects harmful to agricultural and horticultural crops.

In formula (I) the alkyl group represented by R and R' includes straight chain and branched chain alkyl groups having 1 to 5 carbon atoms, for example, a methyl group, an ethyl group, an n-propyl group, an isopropyl group, an n-butyl group, a sec-butyl group, a pentyl group, etc.

The alkyl group represented by R is preferably a methyl group or an ethyl group, and more preferably an ethyl group.

The partial structure represented by A preferably is selected from the member consisting of groups represented by the following formulae:

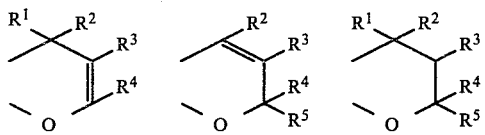

wherein $R^1$, $R^2$, $R^3$, $R^4$ and $R^5$ which may be the same or different, each represents a hydrogen atom or an alkyl group haivng 1 to 5 carbon atoms, preferably a methyl group or an ethyl group.

Insect pests and mites which can be effectively controlled by the compounds of this invention include:

Unhygienic Insects:
    House flies (*Musca domestica vicina*)
    Mosquitoes (*Anophiles sinensis*), (*Culex pipiens pallens*)
    American cockroach (*Peripraneta americana*)
    German cockroach (*Blatteila germanica*)

Insect Pests in Paddy Fields (low land field):
    Rice stem borer (*Chilo suppressalis*)
    Rice stink bug (*Lagymotomus elongatus*)
    Rice leaf beetle (*Oulema oryzae*)
    Rice leaf miner (*Agtomyzae oryzae*)
    Grass leaf roller (*Cnaphalocrocis medinalis*)
    Rice plant skipper (*Parnara guttata*)
    Rice water weevil (*Lissorhoptrus oryzophilus*)
    Rice plant weevil (*Echinocnemus squameus*)

Insect Pests in Upland Farms:
    Tobacco cutworm (*Prodenia litura*)
    cabbage armyworm (*Mamestra brassicae*)
    Diamondback moth (*Plutella xylostella*)
    Green peach aphid (*Myzus persicae sulzer*)

Common cabbage worm (*Pieris rapae crucivora*)
Spiraea aphid (*Aphis spriaccola patch*)
Common cut worm (*Agrotis fucosa*)
Black cut worm (*Agrotis ipsilon*)
Soy bean beetle (*Anomala rufocuprea*)
Japanese beetle (*Popillia japonica*)
Cupreous chafer (*Anomala cuprea*)
Seed maggot (*Hylemya platura*)
Vegetable weevil (*Listroderes obliquus*)
Cucurbit leaf beetle (*Aulacophora femoralis*)
African mole cricket (*Gryllotalpa africana*)
Insect Pests on Tea Trees:
  Tea tortrix (*Homona magnaima*)
  Smaller tea tortrix (*Adoxophyes orana*)
  Tea leaf roller (*Caloptilia theivora*)
  White peach scale (*Pseudoavlacaspis pentagona*)
Insect Pests on Fruit Trees:
  Smaller tea tortrix (*Adoxophyes orana*)
  Comstock mealybug (*Pseudococcus comstocki*)
  Peach pyralid moth (*Dichocrocis punctiferalis*)
  Apple leaf miner (*lithocolletis ringoniella*)
  Mulberry pyralid (*Margaronia pyloalis*)
Insect Pests on Cotton Plants:
  Tobacco budworm (*Heliothis virescence*)
  Boll worm (*Heliothis zea*)
  Boll weevil (*Anthonomus grandis*)
  Pink boll worm (*Pectinophora gossypiella*)
Insect Pests on Lumber:
Mites:
  Termite
  Carmine mite (*Tetranychus cinnabarius*)
  Two spotted spider mite (*Tetranychus urticae*)
  Kanzawa spider mite (*Tetranychus Kanzawai*)
  Citrus red mite (*Panonychus citri*)
  European red mite (*Panonychus ulmi*)
  Bulb mite (*Rhizoglyphus echinopus*)
  Tick
Nematodes:
  Rice white-tip nematode (*Aphelenchoides besseyi*),
  root-knot nematode such as Javanese root-knot nematode (*Meloidogyne javanica*)

Among organic phosphorus compounds of this type, the compounds of the present invention exhibit a high ability to control specifically insect pests, mites, nematodes and unhygienic insects listed above. As the above list indicates the compounds of the present invention are effective against quite a wide variety of insects, mites, etc. Because of this broad insecticidal activity, various insect pests can simultaneously be controlled with each crop treatment, thus reducing the overall costs of protecting the crop. For instance, diamond-back moth, army worms, common cabbage worm, aphids on brassicae; leaf rollers, tea leaf roller, white peach scale on tea trees; apple leaf miner, European red mite, on apple trees and the like can be controlled at one time.

The compounds of the present invention exhibit especially superior effects against leaf miners such as diamond-back moth, apple leaf miner, tea leaf miner and citrus leaf miner.

In general, it is comparatively difficult to control those insect pests which have many number of generation or long breeding seasons and those insect pests which are parasitic to crops. Generally, this means application of chemicals must be preformed many times and in the case of crops this must be done without damaging the crop or making the crop unfit for consumption. The compounds of this invention have extremely long-lasting effects against the above-described noxious organisms, particularly against tea leaf roller, diamond-back moth on vegetables, army worms, soy bean beetles, etc. and they are quite effective at controlling these insect pests with a minimum of applications. Furthermore, because the compounds of the present invention can safely be applied as an emulsifiable concentrate, a wettable powder or s dust directly or as a granule for treating the soil to agricultural crops such as rice, wheat; vegetables, e.g., cabbage, raddish, Chinese cabbage, egg plant, green pepper, tomato, cucumber; beans, e.g., soybeans, kidney beans, adzuki beans, peas; tea leaves; cotton plant; fruit trees, e.g., apple, citrus fruits, pears, kaki (Japanese persimon), peach, grapes; sugar beet; potato, sweet potato, taro; and the like.

Some specific examples of the compounds of the present invention are illustrated in Table below but as a matter of course the present invention is not to be construed as being limited to these compounds.

| Organic Phosphorus Ester Derivatives | | |
|---|---|---|
| Compound No. | Chemical Formula | Physical Property |
| 1 | $CH_3O$, $n\text{-}C_3H_7S$ — P(=O) — O — (aryl with $CH_3$, $CH_3$, $O$, $CH_3$ substituents) | pale yellow liquid<br>b.p. 151° C./0.01 mm Hg<br>$n_D^{20}$ 1.5362 |
| 2 | $C_2H_5O$, $n\text{-}C_3H_7S$ — P(=O) — O — (aryl with $CH_3$, $CH_3$, $O$, $CH_3$ substituents) | colorless viscous liquid<br>b.p. 162–167° C./0.02 mm Hg<br>$n_D^{20}$ 1.5301 |
| 3 | $n\text{-}C_3H_7O$, $n\text{-}C_3H_7S$ — P(=O) — O — (aryl with $CH_3$, $CH_3$, $O$, $CH_3$ substituents) | colorless transparent liquid<br>b.p. 163° C./0.02 mm Hg<br>$n_D^{20}$ 1.5206 |
| 4 | $n\text{-}C_4H_9O$, $n\text{-}C_3H_7S$ — P(=O) — O — (aryl with $CH_3$, $CH_3$, $O$, $CH_3$ substituents) | pale yellow liquid<br>b.p. 166° C./0.01 mm Hg<br>$n_D^{20}$ 1.5218 |

-continued

Organic Phosphorus Ester Derivatives

| Compound No. | Chemical Formula | Physical Property |
|---|---|---|
| 5 | $C_2H_5O$, $n\text{-}C_4H_9S$ — P(=O) — O — [4,4-dimethyl-2-methyl-4H-chromene] | colorless transparent liquid b.p. 167° C./0.01 mm Hg $n_D^{20}$ 1.5259 |
| 6 | $C_2H_5O$, $n\text{-}C_4H_9S$ — P(=O) — O — [4,4-dimethyl-2-methyl-4H-chromene] | pale yellow liquid b.p. 158° C./0.01 mm Hg $n_D^{20}$ 1.5237 |
| 7 | $i\text{-}C_3H_7O$, $i\text{-}C_3H_7S$ — P(=O) — O — [4,4-dimethyl-2-methyl-4H-chromene] | brown liquid b.p. not less than 160° C./0.01 mm Hg $n_D^{20}$ 1.5178 |
| 8 | $C_2H_5O$, $C_2H_5S$ — P(=O) — O — [4,4-dimethyl-2-methyl-4H-chromene] | pale yellow liquid b.p. 148° C./0.01 mm Hg $n_D^{20}$ 1.5319 |
| 9 | $CH_3O$, $n\text{-}C_3H_7S$ — P(=S) — O — [4,4-dimethyl-2-methyl-4H-chromene] | brown liquid b.p. not less than 160° C./0.01 mm Hg $n_D^{20}$ 1.5632 |
| 10 | $C_2H_5O$, $n\text{-}C_3H_7S$ — P(=S) — O — [4,4-dimethyl-2-methyl-4H-chromene] | pale yellow liquid b.p. 155–158° C./0.02 mm Hg $n_D^{20}$ 1.5569 |
| 11 | $C_2H_5O$, $s\text{-}C_4H_9S$ — P(=S) — O — [4,4-dimethyl-2-methyl-4H-chromene] | pale brown viscous liquid b.p. not less than 150° C./0.01 mm Hg $n_D^{20}$ 1.5693 |
| 12 | $C_2H_5O$, $C_2H_5S$ — P(=S) — O — [4,4-dimethyl-2-methyl-4H-chromene] | pale yellow liquid b.p. 148–150° C./0.01 mmHg $n_D^{20}$ 1.5590 |
| 13 | $n\text{-}C_3H_7O$, $CH_3S$ — P(=O) — O — [4,4-dimethyl-2-methyl-4H-chromene] | pale yellow liquid b.p. 165°C./0.05 mm Hg $n_D^{20}$ 1.5344 |
| 14 | $C_2H_5O$, $i\text{-}C_3H_7S$ — P(=O) — O — [4,4-dimethyl-2-methyl-4H-chromene] | colorless transparent liquid b.p. not less than 160° C./0.01 mm Hg $n_D^{20}$ 1.5280 |
| 15 | $s\text{-}C_4H_9O$, $n\text{-}C_3H_7S$ — P(=O) — O — [4,4-dimethyl-2-methyl-4H-chromene] | brown viscous liquid b.p. 154–157° C./0.015 mmHg $n_D^{20}$ 1.5327 |
| 16 | $CH_3O$, $s\text{-}C_4H_9S$ — P(=O) — O — [4,4-dimethyl-2-methyl-4H-chromene] | pale yellow transparent viscous liquid b.p. 154–157° C./0.015 mm Hg $n_D^{20}$ 1.5327 |
| 17 | $C_2H_5O$, $n\text{-}C_3H_7S$ — P(=O) — O — [4,4-dimethyl-2-methyl-chromane] | colorless transparent liquid b.p. 146–149° C./0.01 mm Hg $n_D^{20}$ 1.5188 |

-continued

Organic Phosphorus Ester Derivatives

| Compound No. | Chemical Formula | Physical Property |
|---|---|---|
| 18 | (C₂H₅O)(s-C₄H₉S)P(=O)–O–[4-methyl-2,2-dimethyl-2H-chromene-7-yl] | Orange brown viscous liquid b.p. not less than 180° C./0.01 mm Hg $n_D^{20}$ 1.5435 |
| 19 | (C₂H₅O)(s-C₄H₉S)P(=O)–O–[3,3-diethyl-4-methyl-2-ethyl-2H-chromene-7-yl] | colorless transparent liquid b.p. 170–175° C./0.02 mm Hg $n_D^{20}$ 1.5232 |
| 20 | (C₂H₅O)(n-C₃H₇S)P(=O)–O–[4-methyl-2,2-dimethyl-2H-chromene-7-yl] | orange transparent liquid b.p. 169–172° C./0.015 mm Hg $n_D^{20}$ 1.5416 |
| 21 | (C₂H₅O)(n-C₃H₇S)P(=O)–O–[3,3-diethyl-4-methyl-2-ethyl-2H-chromene-7-yl] | colorless transparent liquid b.p. 164–169° C./0.015 mm Hg $n_D^{20}$ 1.5252 |
| 22 | (C₂H₅O)(n-C₃H₇S)P(=O)–O–[4-methyl-2,2-dimethyl-2H-chromene-5-yl] | pale yellow transparent liquid b.p. 148–150° C./0.025 mm Hg $n_D^{20}$ 1.5373 |
| 23 | (C₂H₅O)(s-C₄H₉S)P(=O)–O–[4-methyl-2,2-dimethyl-2H-chromene-5-yl] | pale yellow transparent liquid b.p. 150–153° C./0.01 mm Hg $n_D^{20}$ 1.5312 |
| 24. | (CH₃O)(n-C₄H₉S)P(=O)–O–[4-methyl-2,2-dimethyl-2H-chromene-7-yl] | pale yellow transparent liquid b.p. 150–151° C./0.03 mmHg $n_D^{20}$ 1.5441 |
| 25. | (CH₃O)(n-C₃H₇S)P(=O)–O–[4-methyl-2,2-dimethyl-2H-chromene-7-yl] | pale yellow transparent liquid b.p. 164–165° C./0.04 mmHg $n_D^{20}$ 1.5470 |

The compounds of the present invention can be prepared by reacting an O-alkyl-S-alkyl thiophosphoric halide of the formula (II) with an aromatic hydroxy compound of formula (III).

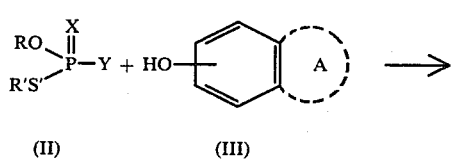

(II)  (III)

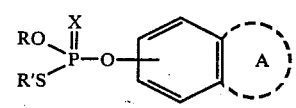

(I)

wherein R, R', X, Y and A have the same meaning as defined above.

The reaction is preferably carried out using an acid acceptor such as tertiary amines, e.g., trialkylamines/-triethylamines, etc.), pyridine, diazabicycloundecene (DBU), dialkylanilines (diethylanilines, etc.), etc.; inorganic bases, e.g., hydrides, hydroxides, carbonates and bicarbonates of alkali metals or alkaline earth metals, for example, sodium hydride, sodium hydroxide, potassium hydroxide, sodium carbonate, potassium carbonate, sodium bicarbonate, potassium bicarbonate, etc.; and the like. The reaction proceeds advantageously using about 0.95 to 1.05 mols of the compounds of the formula (III) and about 0.95 to 1.05 mols of the acid acceptor per mol of the compounds of the formula (II).

Solvents which can be used in this reaction include ethers such as diethyl ether, dipropyl ether, dioxane, tetrahydrofuran, etc., amides such as N,N-dialkylcarboxamides (e.g., N,N-dimethylcarboxamide, etc.), etc., aliphatic, aromatic or halogenated hydrocarbons such as benzene, toluene, xylene, chloroform, chlorobenzene, etc., nitriles such as acetonitrile, dimethyl sulfoxide, ketones such as acetone, methyl ethyl ketone, etc., alcohols such as methanol, ethanol, etc. When reacting compounds in which X represents a sulfur atom water can also be used.

The reaction temperature ranges from about $-10°$ C. to about $50°$ C., preferably at room temperature, in the case of using a tertiary amine as acid acceptor, or from about $-10°$ C. to about $150°$ C., preferably $40°$ to $120°$ C., in the case of using an inorganic base as acid acceptor.

The reaction is performed under these reaction conditions for a period of about 0.5 to about 5 hours, preferably 1 to 2 hours in the case of using a tertiary amine as acid acceptor and about 2 to about 20 hours, preferably 3 to 10 hours in the case of using an inorganic base as acid acceptor, to obtain the desired compounds in high yields.

With respect to the starting material which can be used in the process of the present invention, thiophosphoric halide of the formula (II) is known compound and is available commercially.

Some of the aromatic hydroxy compounds of the formula (III) are known and others are new and can be prepared by condensation reaction of resorcin with an aliphatic ketone.

Representation examples of the aromatic hydroxy compound of formula (III) include the following:

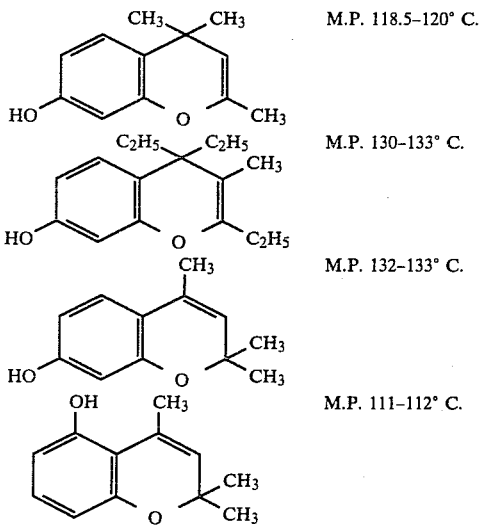

The following Synthesis Examples are provided to illustrate the preparation of some typical compounds of this invention, but they are not to be construed as limiting the present invention. Unless otherwise indicated, all parts, percents, ratios and the like are by weight.

SYNTHESIS EXAMPLE 1

Preparation of Compound No. 2

In 100 ml of toluene was dissolved 19.0 g (0.1 mol) of 2,4,4-Trimethyl-7-hydroxy-1,4-benzopyran and 10.1 g (0.1 mol) of triethylamine and 20.2 g (0.1 mol) of O-ethyl-S-propyl thiophosphoric chloride was added dropwise over a period of 10 minutes to the resulting solution while stirring at 10° to 15° C. After the completion of addition the reaction mixture was stirred at 20° to 25° C. for 3 hours. The triethylamine hydrochloride precipitated was removed by filtration and toluene was distilled off under reduced pressure. The residue obtained was distilled in vacuo to obtain 33.9 g (yield: 95.0%) of O-ethyl-S-propyl-O-(2,4,4-trimethyl-1,4-benzopyran-7-yl)phosphorothioate having the following physical properties.

(1) Refractive Index: $n_D^{20}$ 1.5301
(2) Infrared Absorption Spectral Analysis: $IR_{max}^{liq}$ cm$^{-1}$: 1695 (C=C); 1260 (P=O); 1150, 1030 (P-O-C).

SYNTHESIS EXAMPLE 2

Preparation of Compound No. 7

To 40 ml of acetone was added 9.5 g (0.05 mol) of 2,4,4-trimethyl-7-hydroxy-1,4-benzopyran and 6.5 (0.05 mol) of anhydrous potassium carbonate and 10.8 g (0.05 mol) of O-iso-propyl-S-isopropyl thiophosphoric chloride was added to the mixture with stirring. The resulting mixture was allowed to stand at 40° to 45° C. for 4 hours to effect reaction and the reaction mixture was poured into 200 ml of ice water to separate oily products which were then extracted with toluene. The toluene solution was washed sequentially with water, with an aqueous 5% sodium hydroxide solution and with water, and dried over anhydrous magnesium sulfate. After removing toluene by distillation under reduced pressure the extract was concentrated at 160° C. under a reduced pressure of 0.01 mm Hg to obtain 16 g (yield: 86.5%) of O-isopropyl-S-isopropyl-O-(2,4,4-trimethyl-1,4-benzopyran-7-yl)phosphorothioate having the following physical properties.

(1) Refractive Index: $n_D^{20}$ 1.5178.
(2) Infrared Absorption Spectral Analysis: $IR_{max}^{liq}$ cm$^{-1}$: 1260 (P=O); 980 (P-O-C).

SYNTHESIS EXAMPLE 3

Preparation of Compound No. 9

In 80 ml of benzene were dissolved 9.5 g (0.05 mol) of 2,4,4-trimethyl-7-hydroxy-1,4-benzopyran, 7.6 g (0.05 mol) of DBU and 10.2 g (0.05 mol) of O-methyl-S-propyl dithiophosphoric chloride and the resulting solution was allowed to react at 40° to 45° C. for 3 hours. After the reaction mixture was allowed to cool DBU hydrochloride precipitated was removed by filtration. The filtrate was washed sequentially with water, with an aqueous 5% sodium hydroxide solution and dried over anhydrous magnesium sulfate. After removing benzene under reduced pressure, the residue obtained was further concentrated at 160° C. under a reduced pressure of 0.01 mm Hg to obtain 15 g (yield: 83.8%) of O-methyl-S-propyl-(2,4,4-trimethyl-1,4-benzopyran-7-yl)phosphorodithioate having the following physical properties.

(1) Refractive Index: $n_D^{20}$ 1.5632.
(2) Infrared Absorption Spectral Analysis: $IR_{max}^{liq}$ cm$^{-1}$: 1695 (C=C); 1150, 1030, 995 (P-O-C).

SYNTHESIS EXAMPLE 4

Preparation of Compound No. 16

In 120 ml of methyl ethyl ketone were dissolved 9.5 g (0.05 mol) of 2,4,4-trimethyl-7-hydroxy-1,4-benzopyran and 6.1 g (0.05 mol) of dimethylaniline and 20 ml of methylethyl ketone solution having dissolved therein, 10.1 g (0.05 mol) of O-methyl-S-sec-butyl thiophosphoric chloride was added dropwise to the resulting solution with stirring. After completion of addition the reaction mixture was allowed to stand at 20° to 25° C. for 1 hour and then heated under reflux for 1 hour. After removing solids (dimethylaniline hydrochloride) by filtration, the filtrate was concentrated under reduced pressure. The residual oily product was dissolved in 100 ml of toluene and washed with water. After dehydrating the solution over anhydrous Glauber's salt, toluene was distilled off. Purification of the oily residue by distillation in vacuo afforded 12.2 g (yield: 68.5%) of O-methyl-S-sec-Butyl-O-(2,4,4-trimethyl-1,4-benzopyran-7-yl)phosphorothioate as a pale yellow transparent liquid having a boiling point of 154° to 157° C./0.015 mm Hg.

SYNTHESIS EXAMPLE 5

Preparation of Compound No. 10

To 200 ml of an aqueous 0.1 mol sodium hydroxide solution was added 19.0 g (0.1 mol) of 2,4,4-trimethyl-7-hydroxy-1,4-benzopyran and 21.8 g (0.1 mol) of O-ethyl-S-propyl dithiophosphoric chloride was added dropwise to the resulting mixture at 0° to 5° C. over a period of about 30 minutes with stirring. After the completion of addition, the mixture was allowed to stand at 0° to 5° C. for 1 hour and then at 20° to 35° C. for 4 hours to complete reaction. The oily product precipitated was extracted with 200 ml of benzene. The extract was washed with water until pH of the washings became neutral and dried over anhydrous Glauber's salt. After removal of benzene by distillation, the oily residue was obtained. Purification of the residue by distillation in vacuo afforded 31.6 g (yield: 84.9%) of O-ethyl-S-n-propyl-O-(2,4,6-trimethyl-1,4-benzopyran-7-yl)phosphorodithioate as a pale yellow transparent liquid having a boiling point of 155°-158° C./0.02 mm Hg.

In the same manner as described above, Compound Nos. 3-6, 8, 10, 14 and 15 were prepared.

Also, in the same manner as described above were prepared O-methyl S-sec-butyl O-(2,2,4-trimethyl-1,2-benzopyran-7-yl)phosphorothioate, O-methyl S-n-propyl O-(2,2,4-trimethyl-1,2-benzopyran-7-yl)phosphorothioate, O-methyl S-n-propyl O-(2,4,4-triethyl-3-methyl-1,4-benzopyran-7-yl)-phosphorothioate, O-methyl S-n-propyl O-(2,2,4-trimethyl-1,2-benzopyran-5-yl)phosphorodithioate, O-ethyl S-n-propyl O-(2,2,4-trimethyl-1,2-benzopyran-5-yl)phosphorodithioate and O-ethyl S-sec-butyl O-(2,2,4-trimethyl-1,2-benzopyran-5-yl)phosphorodithioate.

The compounds of the present invention can be applied broadly to upland farms, paddy fields (low land farms), orchards, forests and various non-agricultural lands by suitably selecting the application procedure, the amount of the compound to be used and the like.

A suitable amount of the compound to be applied varies depending upon various factors such as the climatic conditions, the soil conditions, the form of the chemical, the time of application, the method of application, or the types of cultivated crops to which it is applied and the diseases or the insects to be controlled.

When the compounds of this invention are used as an insecticidal, miticidal or nematocidal composition, the compounds can be formulated into various forms such as an emulsifiable concentrate, a wettable powder, a dust, granules, fine granules and other generally employed agricultural preparations by optionally incorporating conventional agriculturally acceptable adjuvants, for example, a carrier such as clay, talc, bentonite, diatomaceous earch or white carbon, solvents such as xylene, toluene, methyl ethyl ketone, isopropanol or dimethyl naphthalene, or a surface active agent such as an alkylbenzenesulfonic acid metal salt, e.g., sodium dodecylbenzenesulfonate, a polyoxyethylene alkylaryl ether, e.g., a polyoxyethylene alkylphenyl ether, a sodium alkylsulfate, a sodium alkylnaphthalenesulfonate, or sodium lignin sulfonate. A suitable ratio of the compounds of this invention to the adjuvant(s) ranges from 0.5:99.5 to 90:10, preferably 1:99 to 70:30 by weight.

The insecticidal, miticidal or nematocidal composition of this invention can also be mixed with other insecticides, miticides and/or nematocides to bring about improved effects.

The above-described preparations are applied to the soil or the stalks and leaves as they are or diluted at a rate of about 0.05 to about 20 kg/ha, preferably 0.15 to 10 kg/ha, more preferably 0.5 to 5 kg/ha, as active ingredient. In case where an emulsifiable concentrate or a wettable powder is used in foliar treatment, it is diluted to a concentration of about 50 to about 2,000 ppm, preferably 100 to 1,000 ppm, more preferably 250 to 500 ppm. In case of application from an airplane, further higher concentrations are employed. That is, a preparation suc as an emulsifiable concentrate and the like is used as it is or diluted with a small amount of water, e.g., 0.5 to 1.5 kg of an emulsifiable concentrate is diluted with 20 to 50 liters of water to obtain a concentration of 10,000 to 75,000 ppm.

The present invention will further be explained more specifically by reference to the following formulation embodiments and examples but the invention is not to be construed as being limited thereto. Unless otherwise indicated, all parts, percents, ratios and the like are by weight.

(a) Emulsifiable Concentrate 5-90%, preferably 20-70%, of active ingredient is dissolved in 5-90%, preferably 30-60%, of a liquid carrier, and 1-40%, preferably 5-20%, of an emulsifying agent is added thereto.

(b) Wettable Powder 5-90%, preferably 20-50%, of active ingredient, 1-20%, preferably 5-10%, of a solid surface active agent, and 5-85%, preferably 40-70%, of a solid carrier are crushed and mixed well.

(c) Dust 0.5-10%, preferably 1-5%, of active ingredient is crushed together with 90-99.5%, preferably 95-99%, of a finely crushed solid carrier.

(d) Granules of Fine Granules 0.5-40%, preferably 2-10%, of active ingredient is sprayed on 60-99.5%, preferably 90-98%, of a solid carrier to adsorb, or the active ingredient is sprayed on a portion of the solid carrier and resulting granules are coated with the rest of the carrier.

FORMULATION EXAMPLE 1

Emulsifiable Concentrate 50 parts of Compound No. 2, 40 parts of xylene and 10 parts of Sorpol SNX (trade name produced by Toho Chemical Co., Ltd.) were uniformly mixed to form an emulsifiable concentrate. Upon use, the concentrate was diluted with water and scattered.

FORMULATION EXAMPLE 2

Emulsifiable Concentrate 50 parts of Compound No. 9, 40 parts of xylene and 10 parts of Sorpol SNX (trade name produced by Toho Chemical Co., Ltd.) were uniformly mixed to form an emulsifiable concentrate. Upon use, the concentrate was diluted with water and scattered.

FORMULATION EXAMPLE 3

Wettable Powder 40 parts of Compound No. 7, 15 parts of diatomaceous earth, 15 parts of clay, 25 parts of white carbon and 5 parts of a mixture of a polyoxyethylene alkylphenyl ether and sodium lignin sulfonate (1:3) were mixed and crushed to obtain a wettable powder.

FORMULATION EXAMPLE 4

Wettable Powder 40 parts of Compound No. 8, 15 parts of diatomaceous earth, 15 parts of clay, 25 parts of white carbon and 5 parts of a mixture of a polyoxyethylene alkylphenyl ether and sodium lignin sulfonate (1:3) were mixed and crushed to obtain a wettable powder.

FORMULATION EXAMPLE 5

Dust 3 parts of Compound No. 10, 47 parts of talc, 47 parts of clay and 3 parts of white carbon were mixed and crushed to obtain a powder. It was scattered as it was upon use.

FORMULATION EXAMPLE 6

Dust 3 parts of Compound No. 5, 47 parts of talc, 47 parts of clay and 3 parts of white carbon were mixed and crushed to obtain a powder. It was scattered as it was upon use.

FORMULATION EXAMPLE 7

Granules 5 parts of Compound No. 13, 15 parts of bentonite, 47.5 parts of talc, 30 parts of clay, 2 parts of sodium lignin sulfonate and 0.5 part of sodium dodecylbenzenesulfonate were uniformly mixed and crushed, and 25 parts of water was added.

FORMULATION EXAMPLE 8

Granules 5 parts of Compound No. 13, 15 parts of bentonite, 47.5 parts of talc, 30 parts of clay, 2 parts of sodium lignin sulfonate and 0.5 part of sodium dodecylbenzenesulfonate were uniformly mixed and crushed, and 25 parts of water was added.

The effects of the compounds according to the present invention will be hereinafter illustrated by way of several test examples. The comparative compounds which were used in these test examples are shown below:

Tokuthion—Trade name of O-(2,4-dichlorophenyl) O-ethyl S-propyl phosphorodithioate manufactured by Nippon Tokushu Noyaku Seizo K.K.

Salithion—Trade name of 2-methoxy-4H-benzo-1,3,2-dioxaphosphorin 2-sulphide manufactured by Sumitomo Chemical Co., Ltd.

Kelthane—Trade name of 2,2,2-trichloro-1,1-bis(4-chlorophenyl)ethanol manufactured by Sankyo Company, Ltd.

Lannate—Trade name of S-methyl N-(methylcarbamoyloxy)thioacetimidate manufactured by Du Pond de Nemours, E. I., and Company.

Dipterex—Trade name of dimethyl 2,2,2-trichloro-1-hydroxyethyl phosphonate manufactured by Nippon Tokushu Noyaku Seizo Co., Ltd.

DDVP—Trade name of dimethyl 2,2-dichlorovinyl dimethyl phosphate manufactured by Nippon Soda Co., Ltd.

Diazinon—Trade name of O,O-diethyl (O-2-isopropyl-6-methyl-pyrimidin-4-yl)phosphorothioate manufactured by Nippon Kayaku Co., Ltd.

Dursban—Trade name of O,O-diethyl O-(3,5,6-trichloro-2-pyridyl)phosphorothioate manufactured by Dow Chemical Company.

Elsan—Trade name of S-($\alpha$-ethoxy-carbonyl benzyl O,O-dimethyl phosphorodithioate manufactured by Nissan Chemicals Co., Ltd.

Orthene—Trade name of O,S-dimethyl acetylphosphoramidothioate manufactured by Chevron Chemical Co.

TEST EXAMPLE 1

Insecticidal Effect on Rice Stem Borer (I) Insecticidal effect on 3rd-instar larvae A wettable powder prepared as described in Formulation Example 3 was diluted with water to a predetermined concentration. Rice seedlings were dipped into the dilute solution and placed in a 60 ml volume cup made of vinyl chloride resin, and 10 3rd-instar larvae of rice stem borer were put in each cup. The cups were capped and maintained at 25° C. After 72 hours, percent mortality was recorded, and the results obtained are shown in Table 1 below.

TABLE 1

| Effective Component (Compound No.) | Concentration (ppm) | Number of Insects Tested | Percent Mortality (%) |
|---|---|---|---|
| 1 | 500 | 60 | 100 |
| 2 | 500 | 60 | 100 |
| 3 | 500 | 60 | 100 |
| 4 | 500 | 60 | 100 |
| 5 | 500 | 60 | 100 |
| 6 | 500 | 60 | 100 |
| 7 | 500 | 60 | 100 |
| 8 | 500 | 60 | 100 |
| 9 | 500 | 60 | 100 |
| 10 | 500 | 60 | 100 |
| 11 | 500 | 60 | 100 |
| 12 | 500 | 60 | 100 |
| 13 | 500 | 60 | 100 |
| 14 | 500 | 60 | 100 |
| 15 | 500 | 60 | 100 |
| 16 | 500 | 30 | 100 |
|  | 100 | 30 | 100 |
| 17 | 500 | 30 | 100 |
|  | 100 | 30 | 100 |
| 18 | 500 | 30 | 100 |
|  | 100 | 30 | 100 |
| 19 | 500 | 30 | 100 |

TABLE 1-continued

| Effective Component (Compound No.) | Concentration (ppm) | Number of Insects Tested | Percent Mortality (%) |
|---|---|---|---|
| | 100 | 30 | 100 |
| 20 | 500 | 30 | 100 |
| | 100 | 30 | 100 |
| 21 | 500 | 30 | 100 |
| | 100 | 30 | 100 |
| 22 | 500 | 30 | 100 |
| | 100 | 30 | 100 |
| 23 | 500 | 30 | 100 |
| | 100 | 30 | 100 |
| Dipterex | 500 | 30 | 100 |
| | 100 | 30 | 100 |
| No Treatment | | 60 | 0 |

TEST EXAMPLE 2

Insecticidal Effect on Tobacco Cutworm

An emulsifiable concentrate prepared as described in Formulation Example 1 was diluted with water to a predetermined concentration and then cabbage leaves were dipped into the dilute solution and dried in air and placed in a 60 ml volume cup made of vinyl chloride resin. 3rd-instar larvae of tobacco cutworm were put in each cup and maintained at 25° C. After 48 hours, percent mortality was assessed. The test was replicated 3 times for each compound using 30 insects in each test. The resulting obtained are shown in Table 2 below.

TABLE 2

| Tested Effective Component (Compound No.) | Concentration (ppm) | Percent Mortality (%) |
|---|---|---|
| 1 | 500 | 100 |
| 2 | 500 | 100 |
| 3 | 500 | 100 |
| 4 | 500 | 100 |
| 5 | 500 | 100 |
| 6 | 500 | 100 |
| 7 | 500 | 100 |
| 8 | 500 | 100 |
| 9 | 500 | 100 |
| 10 | 500 | 100 |
| 11 | 500 | 100 |
| 12 | 500 | 100 |
| 13 | 500 | 100 |
| 14 | 500 | 100 |
| 15 | 500 | 100 |
| 16 | 500 | 100 |
| 17 | 500 | 100 |
| 18 | 500 | 100 |
| 20 | 500 | 100 |
| 22 | 500 | 100 |
| 23 | 500 | 100 |
| Orthene | 500 | 90.0 |
| No Treatment | — | 0 |

TEST EXAMPLE 3

Long-Lasting Insecticidal Effect on Tobacco Cutworm

An emulsifiable concentrate prepared as described in Formulation Example 2 was diluted with water to a predetermined concentration and sprayed onto a cabbage plantlet in a flower pot of 15 cm in diameter using a spray-gun sufficiently and the tests plants were placed in a green house. The leaves of the plants were cut off on the 3rd, 5th, 7th, 10th and 28th day and placed in a 60 ml volume cup and 3rd-instar larvae of tobacco cutworm were put in each cup. The cups were kept in an incubator (25° C.). After 48 hours, percent mortality was assessed. The tests was replicated 3 times for each compound using 30 insects in each test. The results obtained are shown in Table 3 below.

TABLE 3

| Tested Effective Component | Concentration | Percent Mortality After Application | | | | |
|---|---|---|---|---|---|---|
| | | 3rd Day | 5th Day | 7th Day | 10th Day | 15th Day |
| Compound 1 | 500 | 100 | 100 | 100 | 100 | 100 |
| Compound 2 | 500 | 100 | 100 | 100 | 100 | 100 |
| Compound 9 | 500 | 100 | 100 | 100 | 100 | 93.3 |
| Compound 10 | 500 | 100 | 100 | 100 | 100 | 96.7 |
| Compound 16 | 500 | 100 | 100 | 100 | 100 | 100 |
| Compound 17 | 500 | 100 | 100 | 100 | 100 | 53.3 |
| Compound 20 | 500 | 100 | 100 | 100 | 100 | 33.3 |
| Salithion | 500 | 20 | 0 | 0 | 0 | 0 |
| Lannate | 500 | 80 | 30 | 7 | 0 | 0 |
| No Treatment | — | 0 | 0 | 0 | 0 | 0 |

TEST EXAMPLE 4

Insecticidal Effect on Diamond-Back Moth

An emulsifiable concentrate prepared as described in Formulation Example 1 was diluted with water to a predetermined concentration and leaves of a cabbage were dipped into the dilute emulsion for 10 seconds followed by drying in air, and charged in a 60 ml volume cup made of vinyl chloride resin. Then, thirty 3rd-instar larvae of diamond back moth were put in each cup, and the cups were kept at 25° C. After 72 hours, percent mortality was assessed and the test was replicated 3 times for each treatment. The results obtained are shown in Table 4 below.

TABLE 4

| Tested Effective Component (Compound No.) | Concentration (ppm) | Percent Mortality (%) |
|---|---|---|
| 1 | 100 | 100 |
| 2 | 100 | 100 |
| 5 | 100 | 100 |
| 6 | 100 | 100 |
| 9 | 100 | 100 |
| 10 | 100 | 100 |
| 11 | 100 | 100 |
| 16 | 100 | 100 |
| 17 | 100 | 100 |
| 20 | 100 | 100 |
| 22 | 100 | 100 |
| 23 | 100 | 100 |
| DDVP | 500 | 76.7 |
| | 100 | 23.3 |
| No Treatment | — | 0 |

TEST EXAMPLE 5

Insecticidal Effect on Smaller Tea Tortrix

Leaves of an apple tree were dipped into a dilute water suspension of a wettable powder prepared as described in Formulation Example 3. After drying in air, the leaves were charged in a 60 ml volume cup made of vinyl chloride resin, and 30 3rd-instar larvae of smaller tea tortrix were put in each cup. The cups were capped and kept at 25° C. After 72 hours, the number of the surviving insects and the dead insects were recorded to determine percent mortality. In each treatment, 3 cups and 30 insects were used in total. The results are shown in Table 6 below.

TABLE 5

| Tested Effective Component (Compound No.) | Concentration (ppm) | Percent Mortality |
| --- | --- | --- |
| 1 | 100 | 100 |
| 2 | 100 | 100 |
| 9 | 100 | 100 |
| 10 | 100 | 96.7 |
| 14 | 100 | 83.3 |
| 16 | 100 | 100 |
| 17 | 100 | 100 |
| 18 | 100 | 100 |
| 22 | 100 | 100 |
| 23 | 100 | 100 |
| Diazinon | 100 | 43.3 |
| No Treatment | — | 0 |

TEST EXAMPLE 6

Insecticidal Effect on Apple Leaf Miner

A dilute water suspension of a wettable powder prepared as described in Formulation Example 3 was sufficiently sprayed using a spray-gun on a seedling of an apple tree planted in a bisque flower pot to which plant larvea of apple leaf miner just after hatching were parasitic. Thereafter the pots were placed in a green house. Fourteen days after the spraying, bores made by larvae were broken and percent mortality was assessed for all the leaves of each seedling. Three pots were used for each treatment. The results obtained are shown in Table 7 below.

TABLE 6

| Tested Effective Component (Compound No.) | Concentration (ppm) | Number of Tested Insects | Percent Mortality (%) |
| --- | --- | --- | --- |
| 1 | 500 | 85 | 100 |
| 2 | 500 | 67 | 100 |
| 9 | 500 | 61 | 100 |
| 10 | 500 | 91 | 100 |
| 16 | 500 | 102 | 100 |
| 18 | 500 | 98 | 100 |
| 19 | 500 | 77 | 100 |
| 20 | 500 | 86 | 100 |
| 23 | 500 | 79 | 100 |
| Salithion | 500 | 85 | 95 |
| Elsan | 500 | 91 | 13.2 |
| Dursban | 500 | 85 | 29.4 |
| No Treatment | — | 67 | 0 |

TEST EXAMPLE 7

Miticidal Effect on Carmine Mite

An emulsifiable concentrate prepared as described in Formulation Example 1 and diluted to a predetermined concentration was sprayed using a spray-gun on a seedling of a kidney bean placed in a pot of 12 cm in diameter to which plant carmine mites were parasitic. After drying in air, seedlings were kept in a green house, and the number of living insects was recorded on the 7th, 14th, 21st and 28th day from the day of application to determine the control effects. Three pots were used for each treatment. The control effect was assessed by the following formula:

$$\text{Preventive Effect} = \left(1 - \frac{\frac{\Sigma T_{ai}}{T_b}}{\frac{\Sigma C_{ai}}{C_b}}\right) \times 100$$

wherein $\Sigma$ indicates sum and $C_b$, $T_b$, $C_{ai}$ and $T_{ai}$ have the following meanings.

$C_b$: Number of living mites in non-treated sample before applications.

$T_b$: Number of living mites in treated sample before application.

$C_{ai}$: Number of living mites in non-treated sample 7th, 14th, 21st or 28th day from the application.

$T_{ai}$: Number of living mites in treated sample 7th, 14th, 21st or 28th day from the application.

The results obtained are shown in Table 7 below.

TABLE 7

| Tested Effective Component (Compound No.) | Concentration (ppm) | Number of Mites before Application | Number of Living Mites after Application | | | | Control Effect (%) |
| --- | --- | --- | --- | --- | --- | --- | --- |
| | | | 7th Day | 14th Day | 21st Day | 28th Day | |
| 1 | 500 | 58 | 0 | 0 | 0 | 3 | 99.6 |
| 2 | 500 | 86 | 0 | 0 | 0 | 11 | 99.0 |
| 5 | 500 | 49 | 0 | 0 | 16 | 38 | 91.2 |
| 6 | 500 | 77 | 0 | 0 | 4 | 45 | 94.9 |
| 9 | 500 | 63 | 0 | 0 | 0 | 8 | 99.0 |
| 10 | 500 | 70 | 0 | 0 | 2 | 19 | 97.6 |
| Kelthane | 500 | 71 | 0 | 0 | 5 | 12 | 99.0 |
| No Treatment | — | 65 | 128 | 270 | 430 | 781 | — |

TEST EXAMPLE 8

Miticidal Effect on Carmine Mite Resistant to Kelthane

An emulsifiable concentrate prepared as described in Formulation Example 1 and diluted to a predetermined concentration was sprayed using a spray-gun on a seedling of an egg plant placed in a pot of 12 cm in diameter to which plant carmine mites resistant to Kelthane were parasitic. After drying in air, seedlings were kept in a green house, and the number of living insects were recorded on the 7th, 14th, 21st and 28th day from the day of application to determine the control effects. Three pots were used for each treatment. The control effect was assesssed by the formula described in TEST EXAMPLE 7 above. Further, phytotoxicity was observed visually on the 7th day after the application. The results obtained are shown in Table 8 below.

TABLE 8

| Tested Effective Component (Compound No.) | Concentration (ppm) | Number of Mites before Application | Number of Living Mites after Application | | | | Control Effect (%) | Phytotoxicity |
|---|---|---|---|---|---|---|---|---|
| | | | 7th Day | 14th Day | 21st Day | 28th Day | | |
| 1 | 500 | 49 | 0 | 0 | 5 | 11 | 99.0 | — |
| 2 | 500 | 60 | 0 | 0 | 7 | 10 | 99.1 | — |
| 5 | 500 | 51 | 0 | 0 | 9 | 29 | 97.4 | — |
| 6 | 500 | 55 | 0 | 0 | 10 | 54 | 96.4 | — |
| 9 | 500 | 53 | 0 | 0 | 0 | 0 | 100 | — |
| 10 | 500 | 62 | 0 | 0 | 4 | 16 | 99.0 | — |
| 11 | 500 | 63 | 0 | 3 | 10 | 48 | 97.0 | — |
| Kelthane | 500 | 40 | 32 | 0 | 118 | 269 | 61.5 | +++* |
| No Treatment | — | 44 | 75 | 168 | 401 | 774 | 0 | — |

Note:
—None
+Slightly toxic
++Toxic
+++Strongly toxic
*Kelthane caused a strong scorch-like lesion on leaves on the 7th day from the application.

As will be apparent from the result shown in Table 8 above, the compounds of the present invention in which R is different from R' showed an excellent long-lasting effect and found to be useful as a miticidal agent.

TEST EXAMPLE 9

Phytotoxicity on Various Crops

An emulsifiable concentrate prepared as described in Formulation Example 2 was diluted with water to a concentration of 500 ppm based on the effective ingredient and sprayed sufficiently using a spray-gun onto various test plants. The plants were kept in a green house. After 10 days from the application phytotoxicity was checked visually. The test was replicated 3 times for each compound. The results obtained are shown in Table 9 below.

TABLE 9

| Tested Effective Component (Compound No.) | Rice | Apple | Tea | Cabbage | Tomato | Egg Plant | Cucumber | Kidney Bean | Green Pepper | Cotton | Beet |
|---|---|---|---|---|---|---|---|---|---|---|---|
| 1 | — | — | — | — | — | — | — | — | — | — | — |
| 2 | — | — | — | — | — | — | — | — | — | — | — |
| 3 | — | — | — | — | — | — | — | — | — | — | — |
| 4 | — | — | — | — | — | — | — | — | — | — | — |
| 5 | — | — | — | — | — | — | — | — | — | — | — |
| 6 | — | — | — | — | — | — | — | — | — | — | — |
| 7 | — | — | — | — | — | — | — | — | — | — | — |
| 8 | — | — | — | — | — | — | — | — | — | — | — |
| 9 | — | — | — | — | — | — | — | — | — | — | — |
| 10 | — | — | — | — | — | — | — | — | — | — | — |
| 11 | — | — | — | — | — | — | — | — | — | — | — |
| 12 | — | — | — | — | — | — | — | — | — | — | — |
| 13 | — | — | — | — | — | — | — | — | — | — | — |
| 14 | — | — | — | — | — | — | — | — | — | — | — |
| 15 | — | — | — | — | — | — | — | — | — | — | — |
| 16 | — | — | — | — | — | — | — | — | — | — | — |
| 17 | — | — | — | — | — | — | — | — | — | — | — |
| 18 | — | — | — | — | — | — | — | — | — | — | — |
| 19 | — | — | — | — | — | — | — | — | — | — | — |
| 20 | — | — | — | — | — | — | — | — | — | — | — |
| 21 | — | — | — | — | — | — | — | — | — | — | — |
| 22 | — | — | — | — | — | — | — | — | — | — | — |
| 23 | — | — | — | — | — | — | — | — | — | — | — |

Note:
Symbol 79 indicates that no toxicity was observed.

While the invention has been described in detail and with reference to specific embodiments thereof, it will be apparent to one skilled in the art that various changes and modifications can be made therein without departing from the spirit and scope thereof.

What is claimed is:

1. An organic phosphoric acid ester compound represented by the formula (I)

$$\begin{array}{c} RO \\ \phantom{RO}\diagdown \\ \phantom{RO}\phantom{\diagdown}P\text{—O—}\phantom{x} \\ \phantom{RO}\diagup \\ R'S \end{array} \overset{X}{\underset{\|}{\phantom{P}}} \phantom{aa} \begin{array}{c}\text{(Aryl-A)}\end{array} \phantom{aaa} (I)$$

wherein R and R', which may be the same or different, each represents an alkyl group; X represents an oxygen atom or a sulfur atom; and A represents a group of atoms necessary to complete together with the two atoms to which they are attached, a 6-membered heterocyclic ring containing an oxygen atom as the hetero atom, said heterocyclic ring being unsubstituted or substituted with 1 to 5 alkyl groups.

2. The compound of claim 1, wherein said alkyl group represented by R and R' and that as the substituent on the heterocyclic ring represented by A has 1 to 5 carbon atoms.

3. The compound of claim 1 wherein A is selected from the member consisting of groups represented by the following formulae

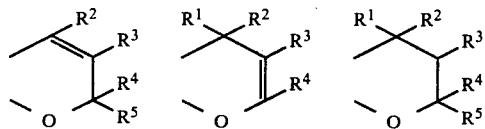

wherein $R^1$, $R^2$, $R^3$, $R^4$ and $R^5$ which may be the same or different, each represents a hydrogen atom or an alkyl group having 1 to 5 carbon atoms.

4. The compound of claim 3 wherein said alkyl group is a methyl group or an ethyl group.

5. The compound of claim 1 wherein said compound is represented by the following formula

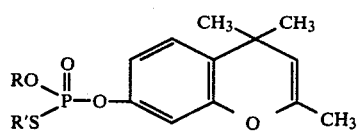

6. The compound of claim 1 wherein said compound is represented by the following formula

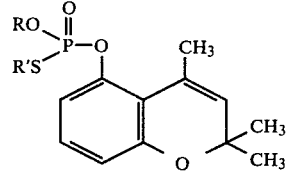

7. The compound of claim 1 wherein R is different from R'.

8. An insecticidal, miticidal or nematocidal composition comprising an insecticidally, miticidally or nematocidally effective amount of at least one organic phosphoric acid ester compound represented by the formula (I):

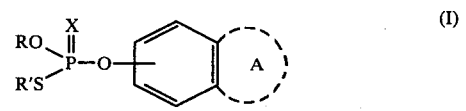

wherein R, R', X and A have the same meaning as in claim 1 as an active ingredient.

9. A process for controlling insects, mites or nematodes which comprises applying to an area or crop subject to said insect, mites or nematodes a composition containing at least one organic phosphoric acid ester represented by the formula (I)

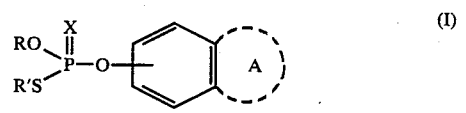

wherein R, R', X and A have the same meaning as in claim 1.

* * * * *

UNITED STATES PATENT AND TRADEMARK OFFICE
CERTIFICATE OF CORRECTION

PATENT NO. : 4,303,653

DATED : December 1, 1981

INVENTOR(S) : ISAO CHIYOMARU, et al

It is certified that error appears in the above-identified patent and that said Letters Patent is hereby corrected as shown below:

On the title page;

Kindly delete "[22] filed: June 27, 1981"

and substitute therefor -- [22] filed: June 27, 1980--.

Signed and Sealed this

Twenty-fourth Day of September 1985

[SEAL]

Attest:

Attesting Officer

DONALD J. QUIGG

Commissioner of Patents and Trademarks—Designate